United States Patent
Kim et al.

(10) Patent No.: US 12,018,111 B2
(45) Date of Patent: Jun. 25, 2024

(54) CORE-SATELLITE MICELLE INCLUDING TETRA-BLOCK COPOLYMER AND PREPARATION METHOD THEREOF

(71) Applicant: POSTECH Research and Business Development Foundation, Pohang-si (KR)

(72) Inventors: Jin Kon Kim, Gyeongju-si (KR); Seonghyeon Ahn, Pohang-si (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 232 days.

(21) Appl. No.: 17/694,883

(22) Filed: Mar. 15, 2022

(65) Prior Publication Data
US 2022/0298284 A1 Sep. 22, 2022

(30) Foreign Application Priority Data
Mar. 22, 2021 (KR) .................. 10-2021-0036412

(51) Int. Cl.
*C08F 293/00* (2006.01)
*A61K 9/107* (2006.01)
(Continued)

(52) U.S. Cl.
CPC .......... *C08F 293/00* (2013.01); *A61K 9/1075* (2013.01); *B01J 13/08* (2013.01);
(Continued)

(58) Field of Classification Search
CPC ............ C08F 293/00; C08F 297/046
See application file for complete search history.

(56) References Cited

FOREIGN PATENT DOCUMENTS

| KR | 10-2012-0057202 | 6/2012 |
| KR | 10-2219498 | 2/2021 |

OTHER PUBLICATIONS

Duan et al. ACS Macromolecule Letters 2017, 6, 257-261 (Year: 2017).*

(Continued)

*Primary Examiner* — Mark S Kaucher
(74) *Attorney, Agent, or Firm* — LEX IP MEISTER, PLLC

(57) ABSTRACT

Proposed are a core-satellite micelle containing a tetra-block copolymer and a preparation method thereof. The core-satellite micelle includes a core, a shell surrounding the core, and a plurality of satellite domains positioned inside the shell. The core-satellite micelle contains a tetra-block copolymer represented by Structural Formula 1 below. The shell includes a first-monomer first block A1 and a first-monomer second block A2, and the satellite domain includes a second-monomer first block B1 and a second-monomer second block B2. The core-satellite micelle is foiled through self-assembly of the tetra-block copolymer, thereby having a larger interfacial contact area than existing block-copolymer micelles. Therefore, the core-satellite micelle can be used in next-generation nanotechnology applications such as drug delivery systems, porous catalyst materials, and sensors.

A1-B1-A2-B2 [Structural Formula 1]

In Structural Formula 1,
A1 is a first-monomer first block,
B1 is a second-monomer first block,
A2 is a first-monomer second block, and
B2 is a second-monomer second block.

20 Claims, 6 Drawing Sheets

(51) Int. Cl.
*B01J 13/08* (2006.01)
*B01J 31/06* (2006.01)
*B01J 35/23* (2024.01)
*B01J 37/00* (2006.01)
*B01J 37/04* (2006.01)
*C08J 5/18* (2006.01)

(52) U.S. Cl.
CPC .............. *B01J 31/063* (2013.01); *B01J 35/23* (2024.01); *B01J 37/0072* (2013.01); *B01J 37/04* (2013.01); *C08J 5/18* (2013.01); *B01J 2231/005* (2013.01); *C08J 2353/02* (2013.01)

(56) References Cited

OTHER PUBLICATIONS

KIPO, Office Action of Application No. 10-2021-0036412, dated Dec. 23, 2022.
Bin Zhao et al., "Emergence and Stability of a Hybrid Lamella-Sphere Structure from Linear ABAB Tetrablock Copolymers", ACS Macro Lett. 2018, 7, 95-99, Dec. 29, 2017.

* cited by examiner

CORE-SATELLITE MICELLE INCLUDING TETRA-BLOCK COPOLYMER AND PREPARATION METHOD THEREOF

CROSS REFERENCE TO RELATED APPLICATION

The present application claims priority to Korean Patent Application No. 10-2021-0036412, filed Mar. 22, 2021, the entire contents of which is incorporated herein for all purposes by this reference.

BACKGROUND OF THE INVENTION

1. Field of the Invention

The present invention relates to a core-satellite micelle including a tetra-block copolymer and a preparation method thereof. More particularly, the present invention relates to a core-satellite micelle prepared through self-assembly of a tetra-block copolymer, the core-satellite micelle having a larger interfacial contact area than existing block copolymer micelles, thereby being applicable to next-generation nanotechnology, such as an effective drug delivery system, a porous catalyst material, and a sensor, and the present disclosure also relates to a preparation method of the same.

2. Description of the Related Art

A block copolymer is defined as a polymer comprising molecules in which two or more different types of polymer blocks coupled by covalent bonds and the polymer blocks interact with each other to form a lamellar, cylindrical, or spherical nanostructure.

When a block copolymer is placed in a solvent that selectively dissolves only one block among the blocks in the block copolymer, the block being phobic to the solvent tries to avoid the solvent, and the block being philic to the solvent tries to contact the solvent, resulting in a core-shell micelle in which the solvent-phobic block forms the core and the solvent-philic block fonts the shell.

The shape of the micellar structure formed of the block copolymer may vary depending on conditions. The block copolymer micelles are mainly core-shell micelles having spherical, cylindrical, or vesicle shapes. Aside from this, extensive research on block copolymer micelles having other shapes has been conducted.

In order to utilize block copolymer micelles in various applications such as drug delivery systems, porous catalyst materials, and sensors, it is required that the block copolymer micelles have a larger interfacial contact area than that of the conventional block copolymer micelles. In addition, there is a problem that the experimental process therefor is complicated and requires precise control.

Therefore, there is a need for research on micelles having a structure having a larger interfacial contact area than conventional block copolymer micelles and on a simple preparation method thereof.

SUMMARY OF THE INVENTION

The present invention has been made to solve the problems occurring in the related art, and an objective of the present invention is to provide micelles having a larger interfacial contact area than conventional block copolymer micelles and a preparation method thereof.

Another objective of the present invention is to provide micelles that can be used in various applications such as drug delivery systems, porous catalyst materials, and sensors, and a preparation method thereof.

A further objective of the present invention is to provide a method of simply preparing micelles having a larger interfacial contact area than conventional block copolymer micelles without requiring complicated processes and precise control.

According to one aspect of the present invention, there is provided a core-satellite micelle including a core, a shell surrounding the core, and a plurality of satellite domains positioned inside the shell. The core-satellite micelle includes a tetra-block copolymer represented by Structural Formula 1 below, and the shell includes a first-monomer first block A1 and a first-monomer second block A2, and the satellite domain includes a second-monomer first block B1 and a second-monomer second block B2.

A1-B1-A2-B2                    [Structural Formula 1]

In Structural Formula 1,
A1 is a first-monomer first block,
B1 is a second-monomer first block,
A2 is a first-monomer second block, and
B2 is a second-monomer second block.

In addition, the satellite domain may surround the core.

In addition, the plurality of satellite domains may form a satellite domain layer.

In addition, the core-satellite micelle may include the first-monomer second block A2 between the core and the satellite domain.

In addition, the core-satellite micelle may include the first-monomer first block A1 between the satellite and a surface of the core-satellite micelle.

In addition, a ratio $V_{B1}/V_{Total}$ of the volume $V_{B1}$ of the second-monomer first block B1 to the volume $V_{Total}$ of the tetra-block copolymer may be in a range of 0.06 to 0.10.

In addition, a volume ratio $V_{A1+A2}:V_{B1+B2}$ of the total volume of the first-monomer first block A1 and the first-monomer second block A2 to the total volume of the second-monomer first block B1 and the second-monomer second block B2 may be in a range of from 40:60 to 60:40.

In addition, the tetra-block copolymer may be a linear block copolymer.

In addition, the first monomer may be different from the second monomer, and the first-monomer first block A1 and the first-monomer second block A2 may not be miscible with the second-monomer first block B1 and the second-monomer second block B2, respectively.

In addition, the first-monomer first block A1 and the first-monomer second block A2 may be each independently include any one segment selected from the segment group consisting of a polyvinylpyrrolidone segment, a polylactic acid segment, a polyvinylpyridine segment, a polystyrene segment, a polytrimethylsilylstyrene segment, a C1-C9 polyalkylene oxide segment, a polybutadiene segment, a polyisoprene segment, a polyolefin segment, and a C1-C5 polyalkyl(meth)acrylate segment. The second-monomer first block and the second-monomer second block may each include another segment selected from the segment group. The former segment may not be miscible with the latter segment.

In addition, the number average molecular weight of the tetra-block copolymer may be in a range of 70,000 to 1,000,000.

In addition, the core-satellite micelle may be for use in a drug delivery system, a porous catalyst material, or a sensor.

According to another aspect of the present invention, there is provided a thin film including the core-satellite micelle.

According to a further aspect of the present invention, there is provided a core-satellite micelle preparation method including: step (a) of preparing a tetra-bock copolymer represented by Structural Formula 1 below from a first monomer, a second monomer, and an initiator; and step (b) of dissolving and stirring the tetra-block copolymer in a solvent.

A1-B1-A2-B2          [Structural Formula 1]

In Structural Formula 1,
A1 is a first-monomer first block,
B1 is a second-monomer first block,
A2 is a first-monomer second block, and
B2 is a second-monomer second block.

In addition, in step (b), the core-satellite micelle may be formed through self-assembly of the tetra-block copolymer.

In addition, each of the first and second blocks A1 and A2 of the first monomer may be soluble in the solvent, and the first and second blocks B1 and B2 of the second monomer may be insoluble in the solvent.

In addition, the first and second blocks A1 and A2 of the first monomer which are soluble in the solvent may form the shell, and the first and second blocks B1 and B2 of the second monomer which are insoluble in the solvent may form the core.

In addition, step (a) includes: step (a-1) of preparing the first-monomer first block A1 by reacting the initiator with the first monomer; step (a-2) of preparing the second-monomer first block B1 by reacting the first-monomer first block A1 with the second-monomer; step (a-3) of preparing the first-monomer second block A2 by reacting the second-monomer first block B1 with the first monomer; and (a-4) of preparing the second-monomer second block B2 by reacting the first-monomer second block A2 with the second monomer to form a second monomer block 2 (B2), thereby preparing the tetra-block copolymer.

In addition, in step (b), the concentration of the solution in which the tetra-block copolymer is dissolved may be in a range of 0.1 to 30 mg/ml.

In addition, the core-satellite micelle preparation method may further include step (c) of applying the solution in which the tetra-block copolymer is dissolved on a substrate and drying the solution to form a thin film including core-satellite micelles, step (c) being performed step (b).

The core-satellite micelle of the present invention has a larger interfacial contact area than conventional block copolymer micelles, thereby being able to be utilized in various applications such as drug delivery systems, porous catalyst materials, and sensors.

In addition, the core-satellite micelle preparation method of the present invention can simply prepare core-satellite micelles having complicated nanostructure forms without requiring complicated processes and precise control.

BRIEF DESCRIPTION OF THE DRAWINGS

Since the accompanying drawings are for reference in describing exemplary embodiments of the present invention, the technical spirit of the present invention should not be construed as being limited to the accompanying drawings.

DESCRIPTION OF THE PREFERRED EMBODIMENTS

Herein after, examples of the present invention will be described in detail with reference to the accompanying drawings in such a manner that the ordinarily skilled in the art can easily implement the present invention.

The description given below is not intended to limit the present invention to specific embodiments. In relation to describing the present invention, when the detailed description of the relevant known technology is determined to unnecessarily obscure the gist of the present invention, the detailed description may be omitted.

The terminology used herein is for the purpose of describing particular embodiments only and is not intended to limit the scope of the present invention. As used herein, the singular forms "a", "an", and "the" are intended to include the plural forms as well unless the context clearly indicates otherwise. It will be further understood that the terms "comprise" or "have" when used in this specification specify the presence of stated features, integers, steps, operations, elements and/or combinations thereof, but do not preclude the presence or addition of one or more other features, integers, steps, operations, elements, and/or combinations thereof.

Terms including ordinal numbers used in the specification, "first", "second", etc. can be used to discriminate one component from another component, but the order or priority of the components is not limited by the terms unless specifically stated. These terms are used only for the purpose of distinguishing a component from another component. For example, a first component may be referred as a second component, and the second component may be also referred to as the first component.

In addition, when it is mentioned that a component is "formed" or "stacked" on another component, it should be understood such that one component may be directly attached to or directly stacked on the front surface or one surface of the other component, or an additional component may be disposed between them.

Hereinafter, a core-satellite micelle including a tetra-block copolymer and a preparation method thereof according to the present invention will be described in detail. However, those are described as examples, and the present invention is not limited thereto and is only defined by the scope of the appended claims.

Figure 1:
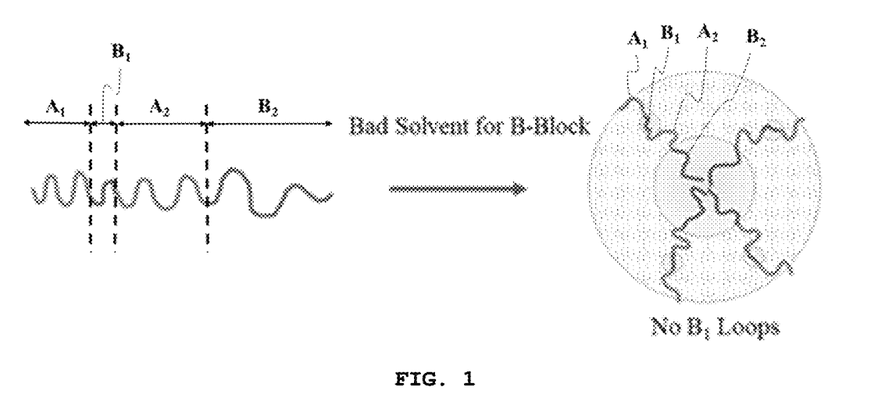
FIG. 1 is a schematic diagram illustrating a core-satellite micelle structure according to an embodiment of the present invention.

FIG. 1 is a schematic diagram illustrating a core-satellite micelle structure according to an embodiment of the present invention;

Referring to FIG. 1, according to the present invention, a core-satellite micelle including a core, a shell surrounding the core, and a plurality of satellite domains positioned inside the shell includes a tetra-block copolymer represented by Structural Formula 1 below, in which the shell includes a first-monomer first block A1 and a first-monomer second block A2, and the satellite domain includes a second-monomer first block B1 and a second-monomer second block B2.

A1-B1-A2-B2　　　　　　　　　　　　　　　　[Structural Formula 1]

In Structural Formula 1,
A1 is a first-monomer first block,
B1 is a second-monomer first block,
A2 is a first-monomer second block, and
B2 is a second-monomer second block.

In addition, the satellite domain may surround the core.

In addition, the plurality of satellite domains may form a satellite domain layer.

In addition, the core-satellite micelle may include the first-monomer second block A2 between the core and the satellite domain.

In addition, the core-satellite micelle may include the first-monomer first block A1 between the satellite and a surface of the core-satellite micelle.

In addition, a ratio $V_{B1}/V_{Total}$ of the volume $V_{B1}$ of the second-monomer first block B1 to the volume $V_{Total}$ of the tetra-block copolymer may be in a range of 0.06 to 0.10, may be preferably in a range of 0.07 to 0.09, and may be more preferably 0.08.

When the ratio $V_{B1}/V_{Total}$ of the volume $V_{B1}$ of the second-monomer first block B1 to the volume $V_{Total}$ of the tetra-block copolymer is less than 0.06, the volume ratio is not preferable because phase separation does not occur due to the small molecular weight of the second-monomer first block B1, and when the ratio $V_{B1}/V_{Total}$ of the volume $V_{B1}$ of the second-monomer first block B1 to the volume $V_{Total}$ of the tetra-block copolymer exceeds 0.10, the volume ratio is not preferable because the second-monomer first block B1 form a loop, so that core-shell micelles similar to conventional double-block copolymer-based core-shell micelles are famed.

Figure 4:
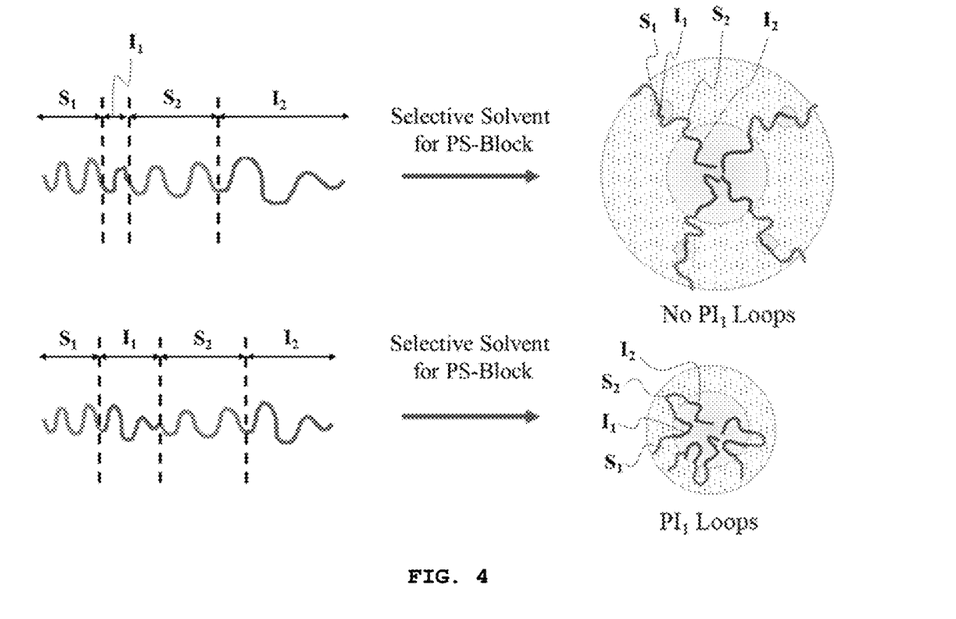
FIG. 4 is a schematic diagram illustrating a tetra-block copolymer structure that may occur in a selective solvent system.

FIG. 4 is a schematic diagram illustrating a tetra-block copolymer structure that may occur in a selective solvent system.

A tetra-block copolymer of polystyrene PS1-polyisoprene PI1-polystyrene PS2-polyisoprene PI2 has a polystyrene selective tends to be structured such that, in a polystyrene-selective solvent, the isoprene blocks PI are positioned inside, and the styrene blocks PS are positioned outside. Thus, the isoprene block PI2 forms the core.

Referring to FIG. 4, when the ratio of the volume $V_{PI1}$ of the isoprene block PI1 to the volume $V_{Total}$ of the tetra-block copolymer is in a range of 0.06 to 0.10, the isoprene blocks exist like satellites due to the strong repulsive force between the isoprene blocks PI and the polystyrene selective solvent (see upper figure in FIG. 4), and when the ratio of the volume $V_{PI1}$ of the isoprene block PI1 to the volume $V_{Total}$ of the tetra-block copolymer exceeds 0.10, the isoprene blocks PI1 form a loop, so that core-shell micelles (lower figure in FIG. 4) similar to conventional double-block copolymer-based core-shell micelles are famed.

In addition, a volume ratio $V_{A1+A2}:V_{B1+B2}$ of the total volume of the first-monomer first and second blocks A1 and A2 to the total volume of the second-monomer first and second blocks B1 and B2 may be in a range of 40:60 to 60:40, may be preferably in a range of 50:50. When the volume ratio $V_{A1+A2}:V_{B1+B2}$ is lower than 40:60 or exceeds 60:40, the volume ratio is not preferable because a spherical micelle structure cannot be formed due to the asymmetric volume ratio between the blocks A1+A2 of the first monomer and the blocks B1+B2 of the second monomer.

In addition, the tetra-block copolymer may be a linear block copolymer.

In addition, the first monomer may be different from the second monomer, and the first-monomer first block A1 and the first-monomer second block A2 may not be miscible with the second-monomer first block B1 and the second-monomer second block B2, respectively.

In addition, the first-monomer first block A1 and the first-monomer second block A2 may be each independently include any one segment selected from the segment group consisting of a polyvinylpyrrolidone segment, a polylactic acid segment, a polyvinylpyridine segment, a polystyrene segment, a polytrimethylsilylstyrene segment, a C1-C9 polyalkylene oxide segment, a polybutadiene segment, a polyisoprene segment, a polyolefin segment, and a C1-C5 polyalkyl(meth)acrylate segment. The second-monomer first block B1 and the second-monomer second block B2 may each include another segment selected from the segment group. The former segment may not be miscible with the latter segment.

Preferably, each of the first and second blocks A1 and A2 of the first monomer may include a polystyrene segment, and each of the first and second blocks B1 and B2 of the second monomer may include a polyisoprene segment that is not miscible with the polystyrene segment.

In addition, the number average molecular weight of the tetra-block copolymer may be in a range of 70,000 to 1,000,000.

In addition, the core-satellite micelle may be for use in a drug delivery system, a porous catalyst material, or a sensor.

The present invention provides a thin film including the core-satellite micelles.

The present invention provides a core-satellite micelle preparation method including: step (a) of preparing a tetra-bock copolymer represented by Structural Formula 1 below from a first monomer, a second monomer, and an initiator; and step (b) of dissolving and stirring the tetra-block copolymer in a solvent.

A1-B1-A2-B2　　　　　　　　　　　　　　　　[Structural Formula 1]

In Structural Formula 1,
A1 is a first-monomer first block,
B1 is a second-monomer first block,
A2 is a first-monomer second block, and
B2 is a second-monomer second block.

In addition, in step (b), the core-satellite micelle may be formed through self-assembly of the tetra-block copolymer.

In addition, each of the first and second blocks A1 and A2 of the first monomer may be soluble in the solvent, and the first and second blocks B1 and B2 of the second monomer may be insoluble in the solvent.

In addition, the first and second blocks A1 and A2 of the first monomer which are soluble in the solvent may form the shell, and the first and second blocks B1 and B2 of the second monomer which are insoluble in the solvent may form the core.

In addition, step (a) includes: step (a-1) of preparing the first-monomer first block A1 by reacting the initiator with the first monomer; step (a-2) of preparing the second-monomer first block B1 by reacting the first-monomer first block A1 with the second-monomer; step (a-3) of preparing the first-monomer second block A2 by reacting the second-monomer first block B1 with the first monomer; and (a-4) of preparing the second-monomer second block B2 by reacting the first-monomer second block A2 with the second monomer to form a second monomer block 2 (B2), thereby preparing the tetra-block copolymer.

In addition, in step (b), the concentration of the solution in which the plurality of tetra-block copolymers is dissolved may be 0.1 to 30 mg/mL, preferably 0.2 to 10 mg/mL, and more preferably 0.5 to 2 mg/ml. When the concentration is lower than 0.1 mg/mL, it is not preferable because it is difficult to form core-satellite micelles due to an insufficient amount of the tetra-block copolymers contained in the solution. On the other hand, when the concentration exceeds 30 mg/mL, it is undesirable because the core-satellite micelles collapse due to aggregation with each other.

In addition, the core-satellite micelle preparation method may further include step (c) of applying the solution in which the tetra-block copolymer is dissolved on a substrate and drying the solution to form a thin film including core-satellite micelles, in which step (c) is performed step (b).

EXAMPLE

Hereinafter, a preferred example of the present invention will be described. However, the example is for illustrative purposes, and the scope of the present invention is not limited thereto.

Preparation Example 1: Preparation of Initiator 1 g of potassium tert-butoxide (8.91 mmol) was dissolved in 10 ml of toluene in a sealed container, and then argon (Ar) was charged into the container to a pressure level higher than atmospheric pressure. Next, 1.4 M of sec-Butyllithium and 2.5 ml of cyclohexane were added to the container while stirring at 25° C. The solution in the container was sufficiently stirred for 10 hours, and it was confirmed that the solution turns dark red. Thus, the initiator was prepared. The preparation reaction of the initiator is as shown in Reaction Formula 1 below.

[Reaction Formula 1]

Preparation Example 2: Preparation of Tetra-Block Copolymer

200 mL of purified tetrahydrofuran was poured into a reactor filled with argon (Ar) at a pressure higher than atmospheric pressure, and the temperature of the reactor was lowered to −78° C. Next, 500 μm of the initiator prepared according to Preparation Example 1 was added to the reactor, and 1.11 g of purified styrene monomer was added to the reactor and sufficiently stirred for 30 minutes to prepare a styrene block PS1. The reaction thereof is as shown in Reaction Formula 2.

[Reaction Formula 2]

After extracting 0.1 ml of a solution containing the styrene block PS1, 0.40 g of purified isoprene monomer was added and stirred sufficiently for 4 hours to form an isoprene block PI1. The reaction is as shown in Reaction Formula 3 below.

[Reaction Formula 3]

Next, after extracting 0.1 ml of a solution containing the styrene block PS1-isoprene block PI1, 1.66 g of purified styrene monomer was added and sufficiently stirred for 30 minutes to form a styrene block PS2. The reaction is as shown in Reaction Formula 4 below.

[Reaction Formula 4]

After extracting 0.1 mL of a solution containing the styrene block PS1-isoprene block PI1-styrene block PS2, 2.20 g of purified isoprene monomer was added and stirred sufficiently for 4 hours. Next, 2 ml of 2-propanol was added and the reaction was completed. Thus, a tetra-block copolymer including the styrene block PS1-isoprene block PI1-styrene block PS2-isoprene block PI2 was prepared. This reaction is as shown in Reaction Formula 5 below.

[Reaction Formula 5]

Preparation Example 3: Preparation of Tetra-Block Copolymer

A tetra-block copolymer was prepared in the same manner as in Preparation Example 2, except that 1.46 g of the isoprene monomer was added instead of 0.40 g of the isoprene monomer when forming an isoprene block PI1.

Example 1: Preparation of Core-Satellite Micelle

The tetra-block copolymer prepared according to Preparation Example 2 was dissolved in diethylphthalate (DEP) at a concentration of 0.5 mg/mL and stirred for one day. Therefore, the tetra-block copolymer was self-assembled to prepare core-satellite micelles.

Example 2: Preparation of Core-Satellite Micelle

Core-satellite micelles were prepared in the same manner as in Example 1, except that dimethylacetamide (DMAc) was used to dissolve the dissolve the tetra-block copolymer instead of the diethylphthalate (DEP).

Comparative Example 1: Preparation of Core-Satellite Micelle

Core-shell micelles were prepared in the same manner as in Example 1, except that the tetra-block copolymer prepared according to Preparation Example 3 was used instead of the tetra-block copolymer prepared according to Preparation Example 2.

Comparative Example 2: Preparation of Core-Satellite Micelle

Core-shell micelles were prepared in the same manner as in Example 1, except that the tetra-block copolymer prepared according to Preparation Example 3 was used instead of the tetra-block copolymer prepared according to Preparation Example 2 and diethylphthalate (DEP) was used as the solvent instead of dimethylacetamide (DMAc).

EXPERIMENTAL EXAMPLE

Experimental Example 1: Characterization of Tetra-Block Copolymers

Figure 2:
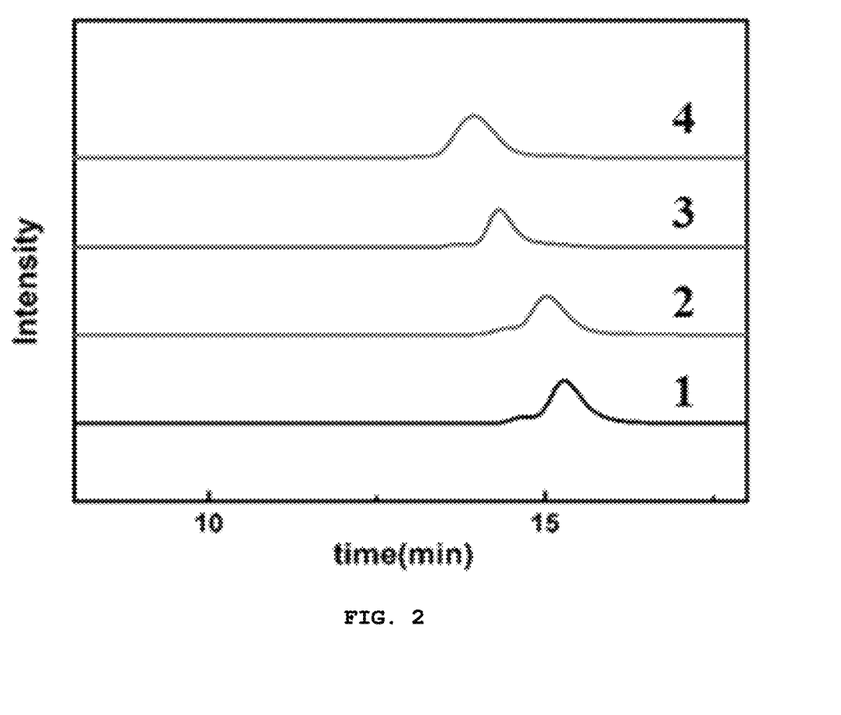
FIG. 2 shows the results of gel permeation chromatography (GPC) of a tetra-block copolymer prepared according to Preparation Example 2.
Figure 3:
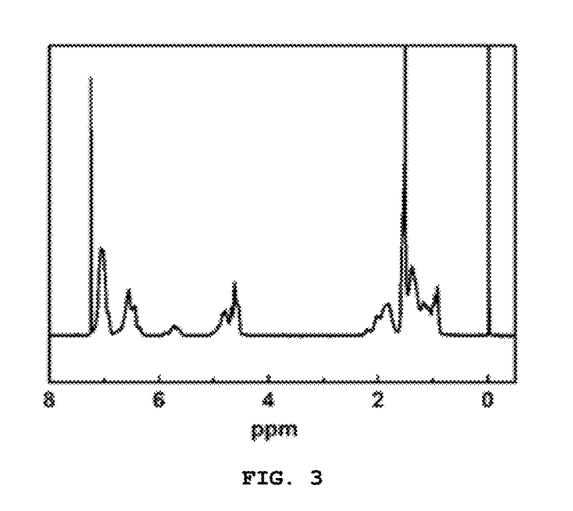
FIG. 3 shows the results of $^1$H NMR of the tetra-block copolymer prepared according to Preparation Example 2.

FIG. 2 shows the results of gel permeation chromatography of the tetra-block copolymer prepared according to Preparation Example 2, and FIG. 3 shows the $^1H$ NMR results of the tetra-block copolymer prepared according to Preparation Example 2.

Referring to FIGS. 2 and 3, the number average molecular weight (Mn) and dispersion degree (PDI, Mw/Mn) of the tetra-block copolymer prepared according to Preparation Example 2, and the total volume fraction $f_{PS}$ of styrene in the tetra-block copolymer, and the volume fractions $f_{PS1}$, $f_{PI1}$, $f_{PS2}$, and $f_{PI2}$ of the respective blocks in the tetra-block copolymer can be identified.

Specifically, the number average molecular weight and dispersion degree of the tetra-block copolymer were measured using gel permeation chromatography (GPC) based on polystyrene (PS), and the volume fraction of each block was calculated using the gel permeation chromatography (GPC) result, the $^1H$ NMR result obtained using a chloroform-d ($CDCl_3$) solvent, and the known densities ($\rho_{PI}$: 0.926, $\rho_{PS}$: 1.05) at room temperature.

The number average molecular weight (Mn) and dispersion degree (PDI, Mw/Mn) of the tetra-block copolymer prepared according to Preparation Example 3, and the total volume fraction $f_{PS}$ of styrene in the tetra-block copolymer, and the volume fractions $f_{PS1}$, $f_{PI1}$, $f_{PS2}$, and $f_{PI2}$ of the respective blocks in the tetra-block copolymer are shown in Table 1 below.

TABLE 1

| Classification | Number average molecular weight Mn (g/mol) | Dispersion degree Mw/Mn | Total volume fraction $f_{PS}$ of styrene | Volume fractions of respective blocks $f_{PS1}$, $f_{PI1}$, $f_{PS2}$, and $f_{PI2}$ |
|---|---|---|---|---|
| Preparation Example 2 | 71900 | 1.15 | 0.54 | 0.22, 0.08, 0.32, and 0.38 |

TABLE 1-continued

| Classification | Number average molecular weight Mn (g/mol) | Dispersion degree Mw/Mn | Total volume fraction $f_{PS}$ of styrene | Volume fractions of respective blocks $f_{PS1}$, $f_{PI1}$, $f_{PS2}$, and $f_{PI2}$ |
|---|---|---|---|---|
| Preparation Example 3 | 61700 | 1.06 | 0.51 | 0.23, 0.20, 0.28, and 0.29 |

Experimental Example 2: Observation of Micelle Structure

FIG. 4 is a schematic diagram illustrating a tetra-block copolymer structure that may occur in a selective solvent system.

Referring to FIG. 4, in the polystyrene selective solvent, the isoprene blocks PI tend to be positioned inside, and the styrene blocks PS tend to be positioned outside. There are two types: relatively large micelles not having a loop form (see upper figure in FIG. 4) and relatively small micelles having a loop form (see lower figure in FIG. 4).

When relatively large micelles were formed, it was observed that the isoprene block PI1 exists like a satellite due to the strong repulsive force between the isoprene block PI and the polystyrene selective solvent. However, when a loop form was famed, it was observed that micelles having a core-shell structure like conventional AB double-block copolymer micelles and being about half the size of the relatively large micelles were formed.

Experimental Example 2-1: Dynamic Light Scattering (DLS) Measurement

Figure 5A:
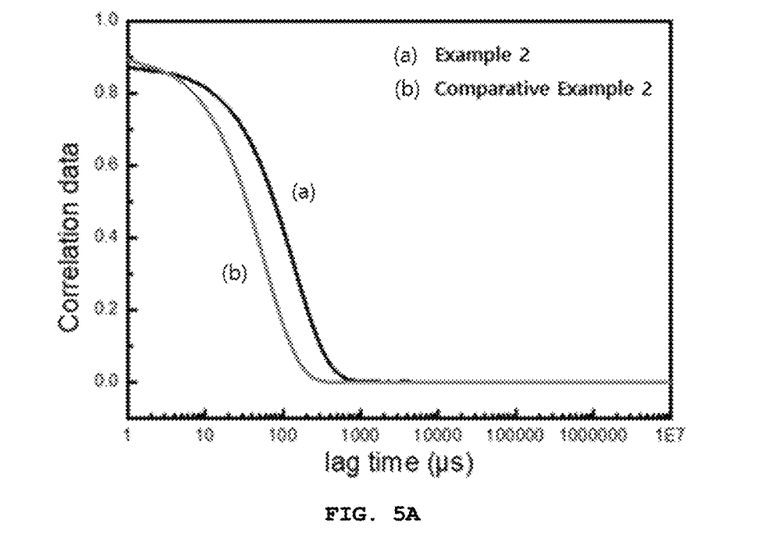
FIG. 5A shows the results of DLS measurement of Example 2 and Comparative Example 2.
Figure 5B:
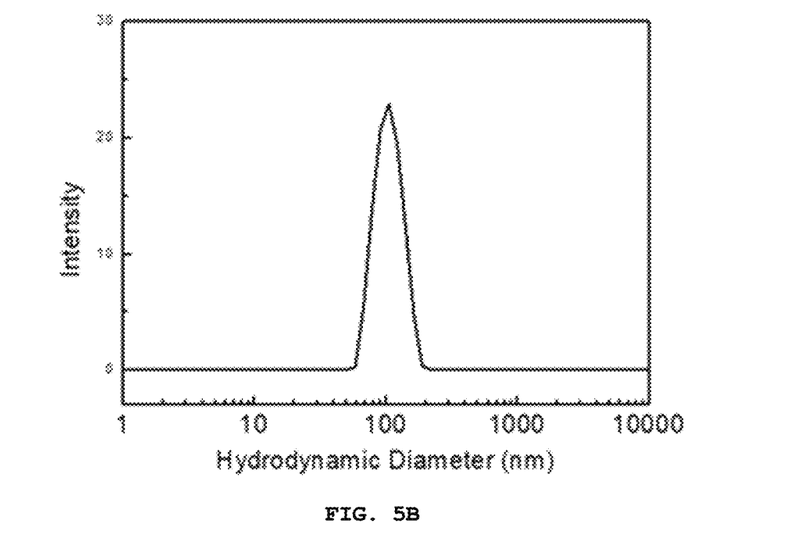
FIG. 5B shows micelle size distribution data obtained from the DLS measurement of Example 2.
Figure 5C:
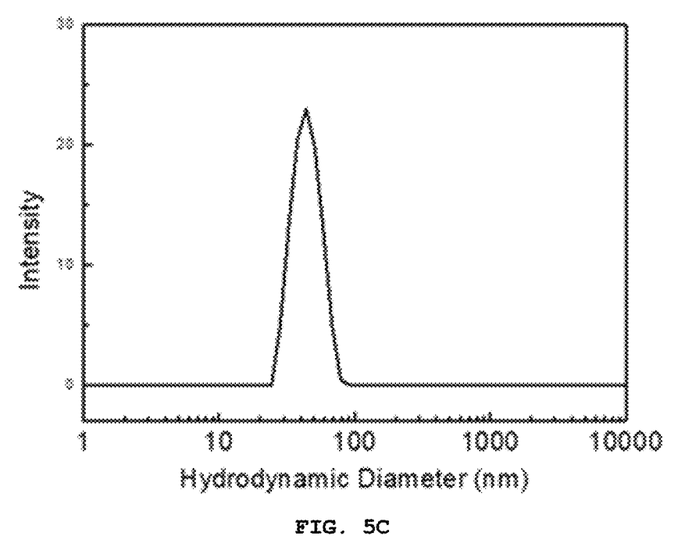
FIG. 5C shows micelle size distribution data obtained from the DLS measurement of Comparative Example 2.

FIG. 5A shows the DLS measurement results of Example 2 and Comparative Example 2, FIG. 5B shows micelle size distribution data obtained from the DLS measurement results of Example 2, and FIG. 5C shows micelle size distribution data obtained from the DLS measurement results of Comparative Example 2.

Referring to FIG. 5A, it is seen that the relaxation time of the micelles prepared according to Example 2 is longer than that of the micelles prepared according to Comparative Example 2, indicating that the micelles prepared according to Example 2 have larger sizes than the micelles prepared according to Comparative Example 2.

Referring to FIGS. 5B and 5C, it is seen that the micelles prepared according to Example 2 have a diameter of 101 nm, and the micelles prepared according to Comparative Example 2 have a diameter of 44 nm.

Although in Example 2 and Comparative Example 2, tetra-block copolymers having similar number average molecular weights were used, it was verified that the size difference between the prepared micelles was more than double. That is, the micelles prepared according to Example 2 did not form a loop configuration and but famed a core-satellite micelle structure, whereas the micelles prepared according to Comparative Example 2 formed a loop configuration, resulting in a core-shell micelle structure.

Experimental Example 2-2: Transmission Electron Microscopy (TEM) Measurement FIG. 6A shows transmission electron microscopy (TEM) measurement results of the micelles prepared according to Example 2, and FIG. 6B shows transmission electron microscopy (TEM) measurement results of the micelles prepared according to Comparative Example 2.

Specifically, 50 µl of the micelles prepared according to Example 2 and 50 µl of the micelles prepared according to Comparative Example 2 were dropped onto a carbon-coated grid, and then the dimethylacetamide (DMAc), which is a solvent, was completely removed with a vacuum pump. Next, vapor of an $OsO_4$ 4 wt. % aqueous solution was used to selectively stain only the isoprene blocks PI, and the micelle was observed through a TEM.

Figure 6A:
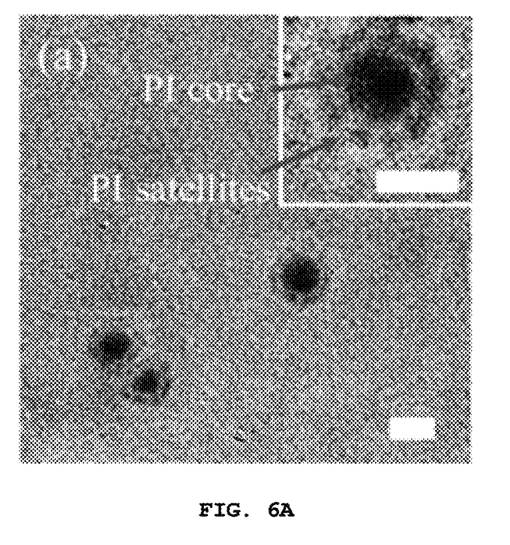
FIG. 6A is a TEM image of a micelle prepared according to Example 2.

Referring to FIG. 6A, it is seen that the micelle prepared according to Example 2 has an isoprene block (PI) core having a diameter of 40 nm and a small isoprene block (PI) satellite structure surrounding the core.

Figure 6B:
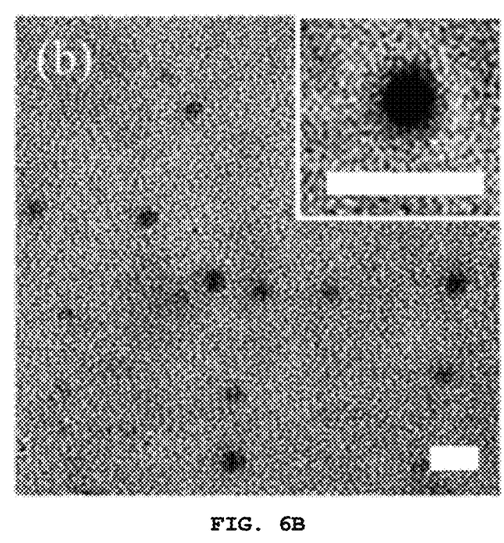
FIG. 6B is a TEM image of a micelle prepared according to Comparative Example 2.

Referring to FIG. 6B, only an isoprene block (PI) core having a diameter of 20 nm is seen in the micelle prepared according to Comparative Example 2. That is, this micelle is a core-shell micelle.

In conclusion, although tetra-block copolymers having similar number average molecular weights are used, when the tetra-block copolymer has a sufficiently long block length, a loop can be formed, resulting in a conventional core-shell micelle structure. On the other hand, when the block length is short, a loop cannot be formed, resulting in a core-satellite micelle structure.

Experimental Example 2-3: Cryo-TEM Measurement

Figure 7A:
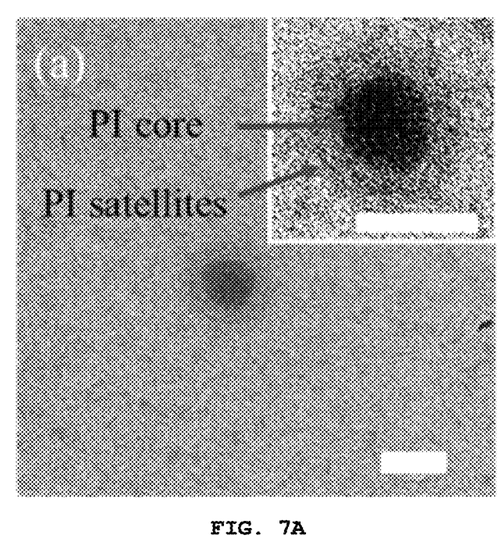
FIG. 7A is a cryo-TEM image of a micelle prepared according to Example 1.
Figure 7B:
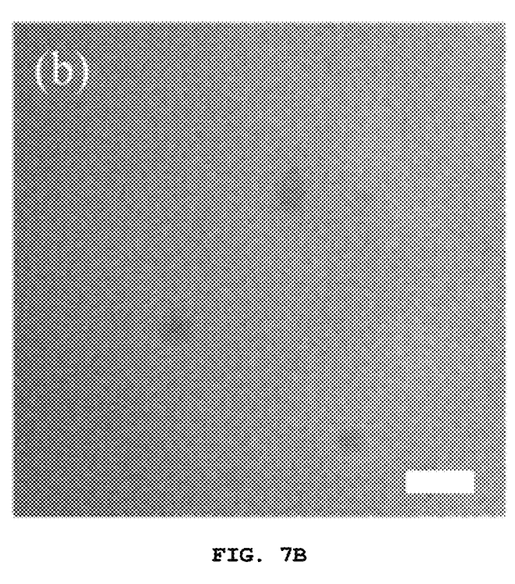
FIG. 7B is a cryo-TEM image of a micelle prepared according to Comparative Example 1.

FIG. 7A shows transmission electron microscopy (TEM) measurement results of the micelles prepared according to Example 1, and FIG. 7B shows transmission electron microscopy (TEM) measurement results of the micelles prepared according to Comparative Example 1.

Specifically, 0.1 mL of an $OsO_4$ 5 wt. % diethyl phthalate solution, which is a solution to selectively stain only isoprene blocks (PI), was added to the diethyl phthalate (DEP) solution containing the micelles prepared according to Example 1 and to the diethyl phthalate (DEP) solution containing the micelles prepared according to Comparative Example 1. Next, a droplet of each of the solutions was dropped on a perforated carbon coated grid. Next, the stain was removed with filter paper, and the grids were put into liquid nitrogen, mounted on cryogenic sample holders, and observed through a cryo-TEM to identify the presence of micelles in the solutions.

Referring to FIGS. 7A and 7B, the micelles prepared according to Example 1 form a core-satellite structure including an isoprene-block (PI) core and small isoprene block (PI) satellites surrounding the core in the solvent. On the other hand, in the case of the micelles prepared according to Comparative Example 1, only a core appears in the solvent. That is, a core-shell structure is formed.

Diethyl phthalate (DEP), which was the solvent used in Example 1 and Comparative Example 1, and dimethylacetamide (DMAc), which was the solvent used in Example 2 and Comparative Example 2, had similar solubility parameters as summarized in Table 2 below. Therefore, it was verified that the form of micelles in diethyl phthalate (DEP) solvent was the same as the form of micelles in dimethylacetamide (DMAc) solvent.

TABLE 2

| Classification | Solubility parameter [MPa$^{1/2}$] |
|---|---|
| Dimethylacetamide (DMAc) | 22.1 |
| Diethyl phthalate (DEP) | 20.5 |
| Styrene block | 17.5 |
| Isoprene block | 15.8 |

The scope of the present invention is defined by the following claims rather than the above detailed description, and all changes or modifications derived from the meaning and scope of the claims and their equivalent concepts should be interpreted as falling into the scope of the present invention.

What is claimed is:

1. A core-satellite micelle comprising a core, a shell surrounding the core, and a plurality of satellite domains disposed inside the shell,
    wherein the core-satellite micelle contains a tetra-block copolymer represented by Structural Formula 1 below,
    the shell contains a first-monomer first block A1 and a first-monomer second block A2,
    the satellite domain contains a second-monomer first block B1, and
    the core contains a second-monomer second block B2, A1-B1-A2-B2                    [Structural Formula 1]

In Structural Formula 1,
    A1 is the first-monomer first block,
    B1 is the second-monomer first block,
    A2 is the first-monomer second block, and
    B2 is the second-monomer second block.

2. The core-satellite micelle according to claim 1, wherein the satellite domains surround the core.

3. The core-satellite micelle according to claim 2, wherein the plurality of satellite domains forms a satellite domain layer.

4. The core-satellite micelle according to claim 1, wherein the core-satellite micelle contains the first-monomer second block A2 between the core and the satellite domain.

5. The core-satellite micelle according to claim 1, wherein the core-satellite micelle contains the first-monomer first block A1 between the satellite and a surface of the core-satellite micelle.

6. The core-satellite micelle according to claim 1, wherein a ratio $V_{B1}/V_{Total}$ of the volume $V_{B1}$ of the second-monomer first block B1 to the volume $V_{Total}$ of the tetra-block copolymer is in a range of 0.06 to 0.10.

7. The core-satellite micelle according to claim 1, wherein a volume ratio $V_{A1+A2}:V_{B1+B2}$ of the total volume of the first-monomer first block A1 and the first-monomer second block A2 to the total volume of the second-monomer first block B1 and the second-monomer second block B2 is in a range of from 40:60 to 60:40.

8. The core-satellite micelle according to claim 1, wherein the tetra-block copolymer is a linear block copolymer.

9. The core-satellite micelle according to claim 1, wherein the first monomer is different from the second monomer, and
    the first-monomer first block A1 and the first-monomer second block A2 are not miscible with the second-monomer first block B1 and the second-monomer second block B2, respectively.

10. The core-satellite micelle according to claim 9, wherein the first-monomer first block A1 and the first-monomer second block A2 is each independently comprise any one segment selected from the segment group consisting of a polyvinylpyrrolidone segment, a polylactic acid segment, a polyvinylpyridine segment, a polystyrene segment, a polytrimethylsilylstyrene segment, a C1-C9 polyalkylene oxide segment, a polybutadiene segment, a polyisoprene segment, a polyolefin segment, and a C1-C5 polyalkyl (meth)acrylate segment,
    the second-monomer first block B1 and the second-monomer second block B2 each comprise another segment selected from the segment group, and
    the former segment contained in the first-monomer first block or the first-monomer second block is not miscible with the latter segment contained in the second-monomer first block or the second-monomer second block.

11. The core-satellite micelle according to claim 1, wherein the tetra-block copolymer may have a number average molecular weight in a range of 70,000 to 1,000,000.

12. The core-satellite micelle according to claim 1, wherein the core-satellite micelle is for use in a drug delivery system, a porous catalyst material, or a sensor.

13. A thin film comprising the core-satellite micelle according to claim 1.

14. A core-satellite micelle preparation method comprising: step (a) of preparing a tetra-bock copolymer represented by Structural Formula 1 below from a first monomer, a second monomer, and an initiator; and step (b) of dissolving and stirring the tetra-block copolymer in a solvent, A1-B1-A2-B2                    [Structural Formula 1]

in Structural Formula 1,
    A1 is a first-monomer first block,
    B1 is a second-monomer first block,
    A2 is a first-monomer second block, and
    B2 is a second-monomer second block.

15. The method of claim 14, wherein in step (b), the core-satellite micelle is formed through self-assembly of the tetra-block copolymer.

16. The method of claim 14, wherein each of the first-monomer first block A1 and the first-monomer second block A2 is soluble in the solvent, and each of the second-monomer first block B1 and the second-monomer second block B2 is not soluble in the solvent.

17. The method of claim 16, wherein the first-monomer first block A1 and the first-monomer second block A2 which are soluble in the solvent form a shell,
    the second-monomer first block B1 which is not soluble in the solvent forms a satellite domain, and
    the second-monomer second block B2 which is not soluble in the solvent forms a core.

18. The method of claim 14, wherein step (a) comprises:
    step (a-1) of preparing the first-monomer first block A1 by reacting an initiator and a first monomer;
    step (a-2) of preparing the second-monomer first block B1 by reacting the first-monomer first block A1 and the second monomer;
    step (a-3) of preparing the first-monomer second block A2 by reacting the second-monomer first block B1 and the first monomer; and
    step (a-4) of preparing the second-monomer second block B2 by reacting the first-monomer second block A2 and the second monomer, thereby preparing the tetra-block copolymer represented by Structural Formula 1 above.

19. The method of claim 14,
    wherein in step (b), the concentration of the solution in which the tetra-block copolymer is dissolved is in a range of 0.1 to 30 mg/ml.

20. The method of claim 14,
further comprising step (c) of applying the solution in which the tetra-block copolymer is dissolved on a substrate and drying the solution to form a thin film comprising the core-satellite micelle on the substrate.

* * * * *